United States Patent
Weiss et al.

(10) Patent No.: US 9,331,360 B2
(45) Date of Patent: May 3, 2016

(54) FLUORIDE ION BATTERY ELECTROLYTE COMPOSITIONS

(75) Inventors: Cedric M. Weiss, Pasadena, CA (US); Simon Christopher Jones, Los Angeles, CA (US); Arunkumar Tiruvannamalai, Monrovia, CA (US); Isabelle Darolles, Los Angeles, CA (US); Maksudul M. Alam, Glendora, CA (US); Sohrab Hossain, Tucson, AZ (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 706 days.

(21) Appl. No.: 12/964,702

(22) Filed: Dec. 9, 2010

(65) Prior Publication Data

US 2011/0143219 A1    Jun. 16, 2011

Related U.S. Application Data

(60) Provisional application No. 61/285,903, filed on Dec. 11, 2009.

(51) Int. Cl.
| | |
|---|---|
| *H01M 10/0566* | (2010.01) |
| *H01M 4/36* | (2006.01) |
| *H01M 10/0569* | (2010.01) |
| *H01M 10/0568* | (2010.01) |
| *H01M 4/583* | (2010.01) |
| *H01M 10/39* | (2006.01) |

(52) U.S. Cl.
CPC ............ *H01M 10/0566* (2013.01); *H01M 4/36* (2013.01); *H01M 4/5835* (2013.01); *H01M 10/0568* (2013.01); *H01M 10/0569* (2013.01); *H01M 10/399* (2013.01); *H01M 2300/0045* (2013.01)

(58) Field of Classification Search
CPC ......... H01M 4/02; H01M 4/06; H01M 4/134; H01M 4/36; H01M 4/5835; H01M 6/14; H01M 6/16; H01M 6/164; H01M 6/166; H01M 10/0568; H01M 10/0569; H01M 10/399; H01M 2300/0045; H01M 10/0566

USPC .......... 429/200, 201, 338, 342, 218.1, 231.6, 429/231.5

See application file for complete search history.

(56) References Cited

U.S. PATENT DOCUMENTS

| | | |
|---|---|---|
| 4,889,659 A | 12/1989 | Genies et al. |
| 7,722,993 B2 | 5/2010 | Potanin |
| 8,377,586 B2 | 2/2013 | Yazami |
| 8,968,921 B2 | 3/2015 | Yazami |
| 2007/0042266 A1 | 2/2007 | Oh et al. |
| 2007/0212615 A1 | 9/2007 | Jost et al. |
| 2008/0020284 A1 | 1/2008 | Michot et al. |
| 2008/0102373 A1 | 5/2008 | Potanin |
| 2009/0253035 A1 | 10/2009 | Otsuki et al. |
| 2010/0221603 A1 | 9/2010 | Yazami et al. |
| 2011/0143219 A1 | 6/2011 | Weiss et al. |
| 2012/0164541 A1 | 6/2012 | Darolles et al. |
| 2013/0122361 A1 | 5/2013 | Yazami |
| 2014/0030559 A1 | 1/2014 | Yazami et al. |

FOREIGN PATENT DOCUMENTS

WO    WO 2011/072166    6/2011

OTHER PUBLICATIONS

Extended European Search Report corresponding to European Patent Application No. 13176816.0, dated Oct. 1, 2013.
Mahjoub et al. (1995) "Reactions of the "Naked" Fluoride Ion: Syntheses and Structures of $SeF_6^{2-}$ and $BrF_6^{1-}$," *Chemistry—A European Journal*, 1:261-265.
Tsuda et al. (2002) "A highly conductive composite electrolyte consisting of polymer and room temperature molten flurohydrogenates," *Solid State Ionics.* 149:295-298.
Chambers, et al. (1999), "Naked fluoride ion from elemental fluorine". Journal of Fluorine Chemistry, vol. 94, pp. 213-215, ISSN 0022-1139. Pp. 214-215.

*Primary Examiner* — Laura Weiner
(74) *Attorney, Agent, or Firm* — Lathrop & Gage LLP

(57) ABSTRACT

A fluoride ion battery includes a substantially lithium-free anode and cathode. At least one of the anode or cathode contains fluorine, and a substantially lithium-free liquid electrolyte is used for charge transport. The electrolyte is liquid at temperatures below about 200 degrees Celsius, and can be formed from an organic-soluble fluoride salt dissolved in selected classes of solvents.

21 Claims, 4 Drawing Sheets

FLUORIDE ION BATTERY ELECTROLYTE COMPOSITIONS

RELATED APPLICATION

This application claims the benefit of U.S. Provisional Application No. 61/285,903, filed Dec. 11, 2009, the disclosure of which is incorporated by reference herein.

FIELD OF THE INVENTION

The present invention relates to non-aqueous electrochemical cells based on fluoride ion transfer, suitable liquid electrolyte compositions containing fluoride ion salts, and to their use in electrochemical cells, including batteries, capacitors, supercapacitors, and galvanic cells.

BACKGROUND AND SUMMARY

A battery generally includes a positive electrode (cathode during discharge), a negative electrode (anode during discharge) and an electrolyte for ion transport. The electrolyte can contain one or more ionic species that that act as charge carriers. Many widely available battery systems are based on cation electrode reactions, with electrodes capturing or releasing a cation from an electrolyte and balancing the charge with an electron from the external circuit. Because of its very low electrochemical oxidation/reduction potential and light weight, the element lithium is commonly used in cation based battery systems. Both lithium and lithium-ion batteries are commercially available and widely used.

However, the electrochemistry of lithium metal or lithium containing electrodes presents problems for commercial use. Lithium metal is highly reactive, and substantial extra processing may be needed to store lithium in safer intercalate, forms, increasing battery weight and reducing energy density. Li-ion batteries are not stable in many situations, and can be easily overheated or overcharged. In extreme cases, this can result in thermal runaway and battery cell rupture, or short circuiting between the electrodes. For safety and to allow for high cycle lifetime, lithium-ion battery packs often contain expensive voltage and thermal control circuitry to shut down the battery when voltage or temperature is outside a safe range.

Anion based electrode reactions offer one solution to the problems associated with lithium and lithium-ion batteries. In an anion based system, the electrode captures or releases an anion from electrolyte, with concomitant release or capture of an electron from the external circuit. Such anion systems have been used in solid state battery systems, for example, by U.S. Pat. No. 7,722,993 to Potanin, which describes an embodiment of a secondary electrochemical cell where fluoride ions are reversibly exchanged between anode and cathode during charge-discharge cycles, with these electrodes in contact with a solid-state fluoride-conducting electrolyte. Potanin describes solid state electrolytes containing fluorides of La, Ce or the compound fluorides based on them together with an alloying additives, such as fluoride/fluorides of alkaline-earth metals ($CaF_2$, $SrF_2$, $BaF_2$) and/or fluorides of alkaline metals (LiF, KF, NaF) and/or alkaline metal chlorides (LiCl, KCl, NaCl), as well as a wide range of other compound fluorides.

Attempts have also been made to provide anion charge carrier based electrochemical systems capable of using liquid electrolytes. For example, US20100221603A1 "Lithium Ion Fluoride Battery" by Yazami, Darolles, and Weiss disclose a battery including a positive electrode comprising a carbon nanofiber or carbon nanotube material; a negative electrode comprising a graphite material; and an electrolyte provided between the positive electrode and the negative electrode. The electrolyte is selected to conduct charge carriers between the positive electrode and the negative electrode, and includes a solvent-borne fluoride salt is at least partially present in a dissolved state in the electrolyte fluoride ions in the electrolyte. In operation, the positive electrode and negative electrode reversibly exchange fluoride ions with the electrolyte during charging and discharging of the battery. In one embodiment, during discharge of the battery fluoride ions are released from the positive electrode and accommodated by the negative electrode, and/or during charging of the battery fluoride ions are released from the negative electrode and accommodated by the positive electrode. However, for many applications the discussed electrolyte compositions are not lithium-free or do not provide sufficient ion transport capability to ensure reliable, high discharge capacity operation.

DETAILED DESCRIPTION

Figure 1:
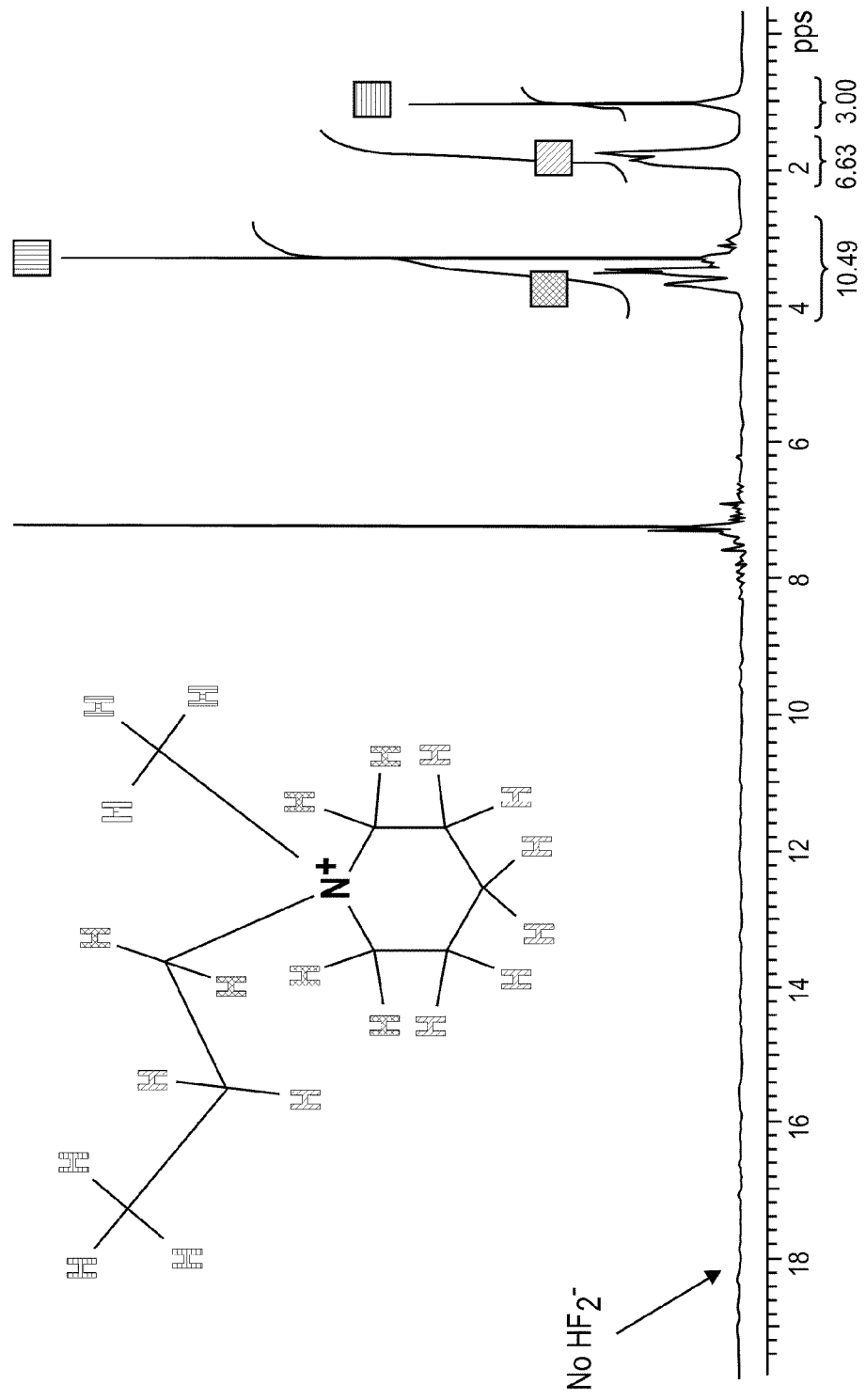
FIG. 1 shows a $^1$H NMR spectrum of MPPF in $C_6D_6$, indicating the presence of MPP$^+$ cation in solution.

To address the foregoing problems, a lithium-free, anion based charge transport electrochemical system that uses fluoride ion transporting electrolytes is described. The fluoride ion transporting electrolyte is typically liquid at temperatures less than 200 degrees Celsius. In other embodiments, electrolytes that remain liquid at less than 100 degrees Celsius are useful. In certain application, low temperature electrolytes that are liquid at temperatures greater than −40 degrees Celsius are preferred. In certain embodiments, primary and secondary (rechargeable) fluoride ion batteries using the foregoing liquid electrolytes and operable at temperatures less than 200 degrees Celsius, or greater than −40 degrees Celsius are described.

A room or low temperature fluoride ion battery (FIB) system utilizes fluoride anions carried in a liquid electrolyte as at least some of the charge carriers in an electrochemical cell. The FIB system has an anode and cathode physically separated from each other, but in common contact with a fluoride anion conducting electrolyte. The anode is typically a low potential element or compound, and can be a metal, metal fluoride, or intercalating composition such as graphite or other carbon based material. Similarly, the cathode can be element or composition, and can be a metal, metal fluoride, or intercalating composition that has a higher potential than the anode. Fluoride anions (F—) in the fluoride conducting electrolyte go from the cathode to the anode during discharge and from the anode to the cathode during the charge of the battery. As will be appreciated, operation of such a fluoride ion battery system requires a ready source of organic soluble free F$^-$ in an electrolyte solution for operation. However, common anhydrous metal fluorides such as alkali or alkaline earth fluorides (e.g. LiF, CsF, $MgF_2$, $BaF_2$), transition metal fluorides (e.g. VF$_4$, FeF$_3$, MoF$_6$, PdF$_2$, AgF), main-group metal fluorides (e.g. AlF$_3$, PbF$_4$, BiF$_3$) and lanthanide or actinide fluorides (e.g. LaF$_3$, YbF$_3$, UF$_5$) are essentially insoluble in organic solvents, so cannot be used as electrolyte components. In addition, many solid-state electrolyte compositions have poor ionic conductivity at temperatures below about 200 degrees Celsius, resulting in significant reduction in cell performance at these lower temperatures due to high cell internal resistance. Such solid-state FIB systems do not generally provide good performance at temperatures below 200 degrees Celsius.

In contrast, liquid electrolytes typically have higher conductivities at room temperatures compared to solid-state electrolytes. This permits FIB systems with liquid electrolytes to operate with lower internal resistances than solid-state systems, improving performance. In addition, liquid electrolyte-based FIB systems will have applicability to areas of operation not possible for solid-state devices, such as reserve battery systems (that are activated by addition of liquid electrolyte to the system) and flexible devices (whereby a solid-state system would crack upon flexing and lose its function).

Primary and secondary anionic electrochemical cells, such as batteries, utilizing fluoride ion charge carriers, active electrode materials, and suitable liquid electrolytes can provide an alternative to conventional state of the art lithium batteries and lithium ion batteries.

In one embodiment, liquid electrolytes suitable use in a fluoride ion electrochemical cell or system include an organic-soluble fluoride salt containing alkylammonium or substituted alkylammonium cations $R^1R^2R^3R^4N^+F^-$ where $R^1$, $R^2$, $R^3$ and $R^4$ may each be separately a substituted or unsubstituted, linear or branched, $C_1$ to $C_{50}$ aliphatic or cyclic aliphatic, fluoroalkyl, oligo(ethyleneglycol), aryl or substituted aryl group.

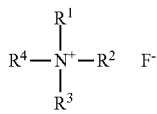

In another embodiment, the organic-soluble fluoride salt is tetramethylammonium fluoride (TMAF) as described in Christe et al., J. Am. Chem. Soc., 1990, 112, 7619, incorporated here by reference.

In another embodiment, the organic-soluble fluoride salt is 2,2-dimethylpropyltrimethylammonium fluoride as described in Mahjoub et al., Chem. Eur. J., 1995, 1, 261, incorporated here by reference.

In another embodiment, the organic-soluble fluoride salt is 1-adamantyltrimethylammonium fluoride as described in Harmon et al., J. Org. Chem., 1993, 58, 7294, incorporated here by reference.

In another embodiment, the organic-soluble fluoride salt is phenyltrimethylammonium fluoride.

In another embodiment, the organic-soluble fluoride salt contains alkylammonium or substituted alkylammonium cations whereby one or more R-group is joined to two or more alkylammonium cations to give a dimer, oligomer or polymer $(R^1R^2R^3R^4N^+)_x(F^-)_x$ where $R^1$, $R^2$, $R^3$ and $R^4$ may each be separately a substituted or unsubstituted, linear or branched, $C_1$ to $C_{50}$ aliphatic or cyclic aliphatic, fluoroalkyl, oligo(ethyleneglycol), aryl or substituted aryl group, and x=2 to 50.

In another embodiment, the organic-soluble fluoride salt is 1,2-bis(dimethylamino)-1,2-bis(dimethylammonium)ethene difluoride as described in Chambers et al., J. Fluorine Chem., 1999, 94, 213, incorporated here by reference.

In another embodiment, the organic-soluble fluoride salt contains alkylguanidinium and substituted alkylguanidinium cations $(R^1R^2N)_3$—$C^+F^-$ where $R^1$, $R^2$, $R^3$ and $R^4$ may each be separately a substituted or unsubstituted, linear or branched, $C_1$ to $C_{50}$ aliphatic or cyclic aliphatic, fluoroalkyl, oligo(ethyleneglycol), aryl or substituted aryl group.

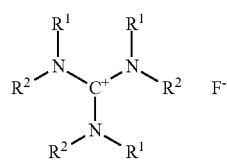

In another embodiment, the organic-soluble fluoride salt is hexamethylguanidinium fluoride as described in Kolomeitsev et al., J. Fluorine Chem., 2000, 103, 159, incorporated here by reference.

In another embodiment, the organic-soluble fluoride salt is of the form $X^+$ $F^-$ where X is a heterocyclic cation, whereby the heterocyclic ring has between 4 and 7 atoms, may be benzoannelated, may be polycyclic and/or may be substituted at one or more positions with a substituted or unsubstituted, linear or branched, $C_1$ to $C_{50}$ aliphatic or cyclic aliphatic, fluoroalkyl, oligo(ethyleneglycol), aryl or substituted aryl groups. Examples of such cations include imidazolium, thiazolium, oxazolium, isoxazolium, pyrazolium, pyridinium, piperidinium, pyrrolidinium, pyrilium, pyridazinium, pyrimidinium, pyrazinium, and triazolium, species.

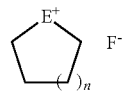

In another embodiment, the organic-soluble fluoride salt is 1-propyl,1-methyl-piperidinium fluoride.

In another embodiment, the organic-soluble fluoride salt is 1,3,3,6,6,-hexamethylpiperidinium fluoride as described in Mahjoub et al., Chem. Eur. J., 1995, 1, 261, incorporated here by reference.

In another embodiment, the organic-soluble fluoride salt is 1-methylhexamethylenetetramine fluoride as described in Gnann et al., J. Am. Chem. Soc., 1997, 119, 112, incorporated here by reference.

In another embodiment, the organic-soluble fluoride salt is a phosphazene or phosphazenium-containing material such as 1,1,1,3,3,3-hexakis(dimethylamino)diphosphazenium fluoride and tetrakis[tris(dimethylamino)-phosphoranylidenamino]phosphonium fluoride as described in Schwesinger et al., Chem. Eur. J., 2006, 12, 438, incorporated here by reference.

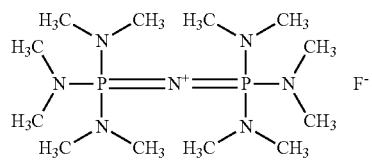

In another embodiment, the organic-soluble fluoride salt contains alkylphosphonium or substituted alkylphosphonium cations $R^1R^2R^3R^4P^+F^-$ where $R^1$, $R^2$, $R^3$ and $R^4$ may each be separately a substituted or unsubstituted, linear or branched, $C_1$ to $C_{50}$ aliphatic or cyclic aliphatic, fluoroalkyl, oligo(ethyleneglycol), aryl or substituted aryl group.

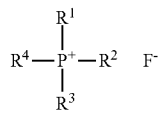

In another embodiment, the organic-soluble fluoride salt is tetramethylphosphonium fluoride, as described in Komath et al., Inorg. Chem., 2003, 42, 2894, incorporated here by reference.

In another embodiment, the organic-soluble fluoride salt is tetraphenylphosphonium fluoride, as described in Brown et al., J. Chem. Soc., Chem. Commun, 1983, 1256, incorporated here by reference.

In another embodiment, the organic-soluble fluoride salt is phenyltrimethylphosphonium fluoride.

In another embodiment, the organic-soluble fluoride salt contains a cation that is a polymer species such as $[Z\text{-Het}^+\text{-}X\text{-Het}^+\text{-}]_n$, whereby Het is a heterocyclic cation whereby the heterocyclic ring has between 4 and 7 atoms, may be benzoannelated, may be polycyclic and/or may be substituted at one or more positions with a substituted or unsubstituted, linear or branched, $C_1$ to $C_{50}$ aliphatic or cyclic aliphatic, fluoroalkyl, oligo(ethyleneglycol), aryl or substituted aryl groups, and Z and X are spacer group such as $CH_2$, $CMe_2$, $SiMe_2$, $SO_2$, $P=O$, $C_2$ to $C_{50}$ aliphatic or cyclic aliphatic, fluoroalkyl, oligo(ethyleneglycol), aryl or substituted aryl groups, and may be the same or different from each other.

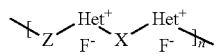

In another embodiment, the organic-soluble fluoride salt is poly(1,1-dimethyl-3,5-dimethylene piperidinium)fluoride, as described in Rios et al., J. Poly. Sci. B. Poly. Phys., 1990, 28, 505, incorporated here by reference.

Solvents useful in this invention include those that are non-aqueous (denoted here as "organic") and are capable of dissolving the aforementioned fluoride salts to molar concentrations of 0.01 M and above, with preferred concentrations being between 0.05 and 5 M. These can include nitriles, amines, ethers, carbonates, nitro compounds, aliphatic and aromatic hydrocarbons, halogenated compounds, sulfoxides, sulfones, amides, esters, alcohols, heterocyclic compounds, linear and cyclic molecules containing one or more of these functional groups. Examples of such solvents include acetone, acetonitrile, benzonitrile, 4-fluorobenzonitrile, pentafluorobenzonitrile, triethylamine, diisopropylethylamine, 1,2-dimethoxyethane, ethylene carbonate, propylene carbonate, γ-butyrolactone, dimethyl carbonate, diethyl carbonate, methyl ethyl carbonate, propyl methyl carbonate, tetrahydrofuran, 2-methyltetrahydrofuran, nitromethane, benzene, toluene, chloroform, dichloromethane, 1,2-dichloroethane, dimethylsulfoxide, sulfolane, N,N-dimethylformamide, N,N-dimethylacetamide, carbon disulfide, ethyl acetate, methyl butyrate, n-propyl acetate, methyl propionate, methyl formate, 4-methyl-1,3,-dioxolane, pyridine, methyl isobutyl ketone, methyl ethyl ketone, hexamethylphosphoramide, hexamethylphosphorus triamide, 1-methyl-2-pyrrolidinone, 2-methoxyethyl acetate, and substituted derivatives thereof, as well as sulfones such as ethylmethylsulfone, trimethylene sulfone, 1-methyltrimethylene sulfone, ethyl-sec-butyl sulfone, 3,3,3-trifluoropropylmethyl sulfone and 2,2,2-trifluoroethyl sulfone A wide range of electrode materials can be used in conjunction with the described liquid electrolytes. To improve safety, lithium-free electrodes, or substantially lithium-free, or electrodes with low weight percentage lithium (for example, less than 10 percent lithium) are preferred.

Anode Materials:

Any metal M of the periodic table in the charged state or corresponding metal fluoride $MF_n$ in the discharged state having a standard potential $E_0$ lower than the standard potential of the cathode material. n being larger than zero.

Any alloy of any metals $MM_1M_2 \ldots M_n$ in the charged state or corresponding alloy metal fluoride $MM_1M_2 \ldots M_nF_m$ in the discharged state having a $E_0$ lower than the $E_0$ of the cathode material.

Any metal fluoride $MF_n$ in the charged state that can undergo a further fluorination to $MF_{n+x}$ or $MF_{n+x}$ in the discharged state that has an intermediate fluorination state (metal oxidation state higher than zero) having a standard potential lower than the cathode material.

Any metal oxide $MO_x$ in the charged state or corresponding metal oxide fluoride $MO_xF_n$ in the discharged state having a standard potential $E_0$ lower than the standard potential of the cathode material.

Any alloy $MM_1M_2 \ldots M_nO_xF_m$ with n larger or equal to 2 and m being larger or equal to zero.

Any polymer that can accommodate fluoride anions in its structure having a standard potential $E_0$ lower than the standard potential of the cathode material including (but not limited to) polyaniline or polypyrrole.

Any LDH (Layered Double Hydroxide) that can accommodate fluoride anions into its structure having a standard potential $E_0$ lower than the standard potential of the cathode material. General formula: $M^{z+}_{1-x}M^{3+}_x(OH)_2]^{q+}(X^{n-})_{q/n} \cdot yH_2O$ Any mixture of one or more of the above mentioned type of materials.

Cathode Materials:

Any metal M of the periodic table in the discharged state or corresponding metal fluoride $MF_n$ in the charged state having a standard potential E0 larger than the standard potential of the anode material. n being larger than zero.

Any alloy of any metals $MM_1M_2 \ldots M_n$ in the discharged state or corresponding alloy metal fluoride $MM_1M_2 \ldots M_nF_m$ in the charged state having a E0 larger than the E0 of the anode material.

Any metal fluoride $MF_n$ in the discharged state that can accommodate more fluorine to $MF_{n+x}$ or $MF_{n+x}$ in the charged state that has an intermediate fluorination state (metal oxidation state higher than zero) having a standard potential larger than the anode material.

Any metal oxide $MO_x$ in the discharged state or corresponding metal oxide fluoride $MO_xF_n$ in the charged state having a standard potential $E_0$ larger than the standard potential of the anode material.

Any metal oxide $MO_xF_n$ in the discharged state or further fluorinated metal oxide fluoride $MO_xF_{n+x}$ in the charged state having a standard potential $E_0$ larger than the standard potential of the anode material.

Any alloy $MM_1M_2 \ldots M_nO_xF_m$ with n larger or equal to 2 and m being larger or equal to zero.

Any polymer that can accommodate fluoride anions in its structure having a standard potential $E_0$ larger than the standard potential of the anode material including (but not limited to) polyaniline or polypyrrole.

Any LDH (Layered Double Hydroxide) that can accommodate fluoride anions into its structure having a standard potential $E_0$ larger than the standard potential of the anode material. General formula: $M^{2+}_{1-x}M^{3+}_{x}(OH)_2]^{q+}(X^{n-})_{q/n} \cdot yH_2O$ Any mixture of one or more of the above mentioned type of materials.

$CF_x$ carbon fluoride with x being between zero and 2.

Examples of Theoretical Standard Potentials for Some Electrode Materials:

To better understand one example of a fluoride ion electrochemical system, consider:

$La/F^-$ electrolyte/$CoF_3$

Having extended cell reaction:

$$La + CoF_3 \leftrightarrow LaF_3 + Co \qquad \text{Eq. 1}$$

From the following Table 1 which lists representative anode (Ca, Ce, La, and Ba) and cathode ($BiF_3$, $CuF_2$, $CoF_3$, $SnF_2$, $NiF_2$ and $FeF_3$) materials for the FIB with their standard potential and its capacity; along with Eq. 1, voltage and the theoretical energy density of the system for selected anode/cathode pairs can be calculated as follows in Table 2:

TABLE 1

|  | $E_0$ (V) vs Li | Capacity (mAh/g) |
|---|---|---|
| Ca | 0 | 1340 |
| Ce | 0.1 | 574 |
| La | 0.1 | 579 |
| Ba | 0.1 | 390 |
| $BiF_3$ | 3 | 303 |
| $CuF_2$ | 3.6 | 528 |
| $CoF_3$ | 3.6 | 694 |
| $SnF_2$ | 3 | 342 |
| $NiF_2$ | 3 | 554 |
| $FeF_3$ | 2.7 | 712 |

TABLE 2

| Anode/cathode | Specific Energy (Wh/kg) | Energy density (Wh/L) |
|---|---|---|
| La/$CoF_3$ | 1100 | 5400 |
| Ca/$CoF_3$ | 1650 | 5600 |
| La/$CuF_2$ | 970 | 4800 |
| Ca/$CuF_2$ | 1360 | 3870 |
| La/$BiF_3$ | 580 | 3200 |

Using the described electrodes and electrolytes, along with conventional separators, battery casing or packaging, current collectors, electrical contacts, and other elements of battery construction known to those skilled in the art, one can create useful electrochemical cells operable at less than 200 degrees Celsius. Such electrochemical cells can have substantially irreversible electrochemical reactions during discharge, making them suitable for forming galvanic cells or primary batteries. Alternatively, if the electrochemical reaction is at least partially reversible through application of electrical charge, secondary (rechargeable) batteries can be formed. Alternatively, capacitors and supercapacitors can be formed.

In some embodiments, electrolytes that remain liquid at less than 100 degrees Celsius are useful. In certain applications, low temperature electrolytes that are liquid at temperatures greater than −40 degrees Celsius are preferred. In certain embodiments, primary and secondary (rechargeable) fluoride ion batteries using the described liquid electrolytes can be operable at temperatures less than 100 degrees Celsius, or greater than −40 degrees Celsius.

The following specific examples are given to illustrate the practice of the invention, but are not to be considered as limiting in any way.

EXAMPLE 1

Preparation of 1-methyl,1-propyl-piperidinium fluoride. 1-methyl,1-propylpiperidinium bromide was synthesized by adding 1-bromopropane (28.8 g, 0.21 mol) drop-wise into N-methylpiperidine (21.1 g, 0.21 mol) dissolved in acetonitrile (150 mL) The precipitated 1-methyl,1-propylpiperidinium bromide was filtered, washed with acetonitrile (5×10 mL) and dried in vacuum. 1-methyl,1-propylpiperidinium bromide (1 g, 5 mmol) was dissolved in $H_2O$ (20 mL) To this solution was added a solution of AgF (0.51 g, 4 mmol) in $H_2O$ (20 mL) over 30 minutes, resulting in the precipitation of AgBr as a yellow solid. The mixture was filtered and the filtrate was dried on a rotary evaporator (keeping the temperature below 50° C.) to afford a white solid, hereafter designated MPPF.

Yield 0.7 g, 4 mmol, 95%.

EXAMPLE 2

Figure 2:
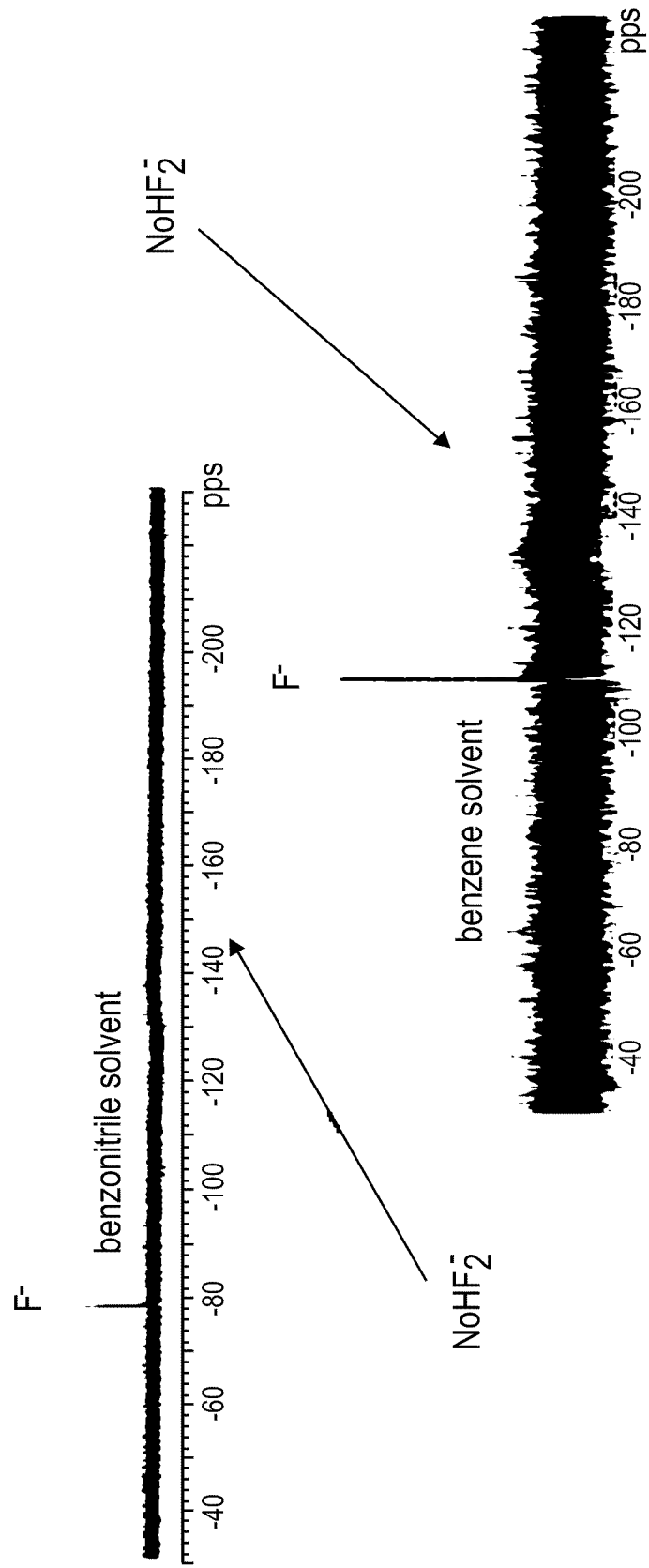
FIG. 2 shows $^{19}$F NMR spectra of MPPF in benzonitrile and $C_6D_6$, indicating the presence of F$^-$ anion in solution, and the absence of any $HF_2^-$ impurity.

NMR spectroscopy. 0.05 g MPPF was dissolved in 1 mL dry $C_6D_6$ in an Ar-filled glovebox, and investigated by $^1H$ and $^{19}F$ NMR spectroscopy. FIG. 1 shows the $^1H$ NMR spectrum, indicating the presence of $MPP^+$ cation in stable form. FIG. 2 shows the $^{19}F$ spectrum, indicating the presence of $F^-$ ion in solution, at similar chemical shift to that observed for other "naked" fluoride ions in $C_6D_6$ solution described in Schwesinger et al., Chem. Eur. J., 2006, 12, 438. No impurity peaks due to HF or $HF_2^-$ were observed in this spectrum.

EXAMPLE 3

Figure 3:
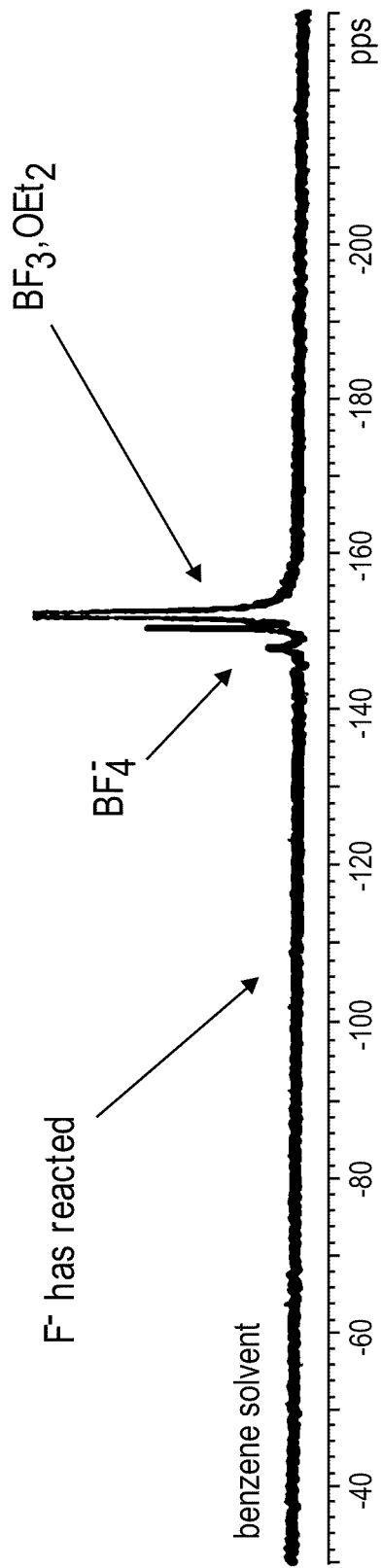
FIG. 3 shows a $^{19}$F NMR spectrum of the reaction product of MPPF with $BF_3.OEt_2$ in $C_6D_6$, the presence of $BF_4^-$ indicating the reactivity of MPPF as a fluoride source.

Reactivity of MPPF in solution. To the solution of MMPF in $C_6D_6$ described in Example 2 was added ~0.1 mL $BF_3 \cdot OEt_2$ in dry $Et_2O$. $^{19}F$ NMR spectroscopy shown in FIG. 3 indicated the quantitative consumption of $F^-$ to give $BF_4^-$, thus demonstrating the reactivity of the $F^-$ ion in organic solution.

EXAMPLE 4

Solubility. MPPF was found to dissolve in several organic solvents, including chloroform, benzonitrile, propylene carbonate, and an ethylene carbonate (EC)/dimethyl carbonate (DMC) mixture (1:1 vol./vol.).

EXAMPLE 5

Conductivity data. MPPF was dissolved at several concentrations in a mixture of EC and dimethyl carbonate DMC (1:1 vol./vol.). Conductivity data was measured using a two-electrode conductivity cell. The conductivity value measured was 2.2 mS/cm (0.1 M solution).

EXAMPLE 6

Conductivity data. TMAF was dissolved at several concentrations in a mixture of EC and propylene carbonate (PC) (1:1 vol/vol). Conductivity data was measured using a two-electrode conductivity cell. The conductivity value measured was 1.7 mS/cm (0.1 M solution).

EXAMPLE 7

Figure 4:
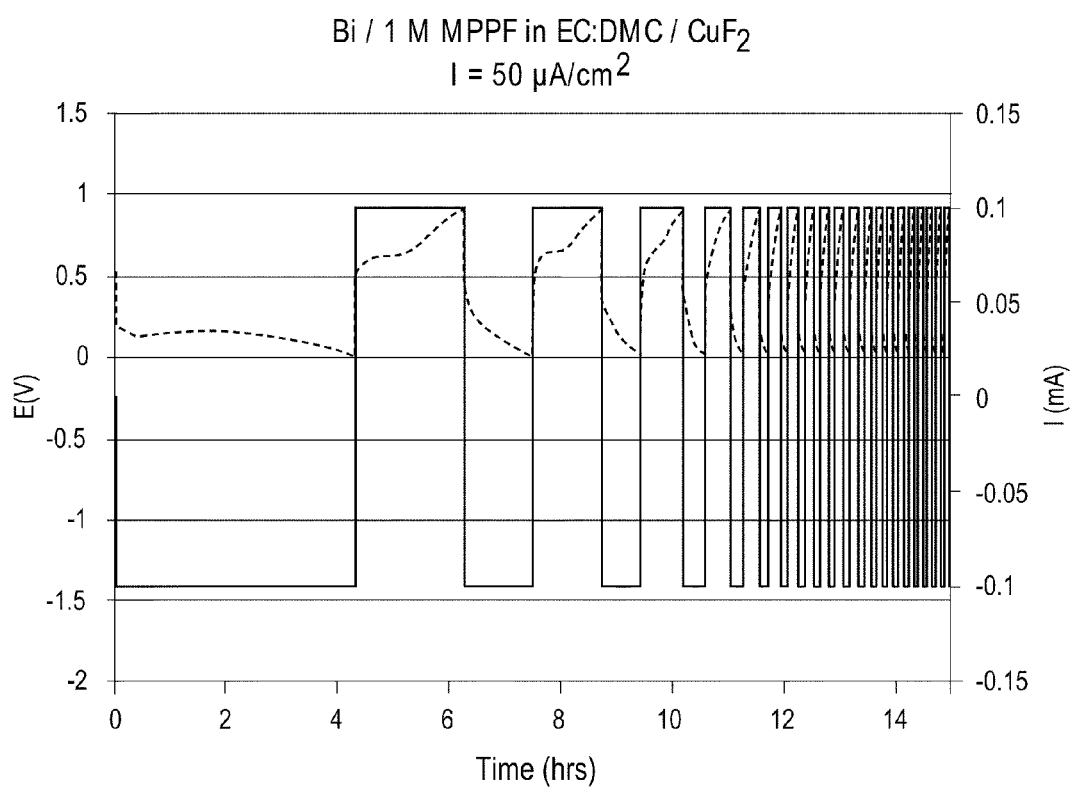
FIG. 4 shows cycling of a full cell with bismuth as the anode, copper fluoride as the cathode and a 1M MPPF solution in EC:DMC.

Cell Operation. FIG. 4 shows cycling of a full cell with bismuth as the anode, copper fluoride as the cathode and a 1M MPPF solution in EC:DMC. This indicates superior cell performance with suitable electrolytes and exemplary electrodes.

All references throughout this application, for example non-patent literature documents or other source material; are hereby incorporated by reference herein in their entireties, as though individually incorporated by reference, to the extent each reference is at least partially not inconsistent with the disclosure in this application The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed in various embodiments; optional features, modification and variation of the concepts herein disclosed may be resorted to by those skilled in the art, and such modifications and variations are considered to be within the scope of this invention as defined by the claims. As will be understood by one of skill in the art, methods and devices useful for the present methods can include a large number of optional composition and processing elements and steps. When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. Many of the molecules disclosed herein contain one or more ionizable groups. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt. Every formulation or combination of components described or exemplified herein can be used to practice the invention, unless otherwise stated. Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the following claims.

What is claimed is:

1. A fluoride ion battery comprising:
lithium-free electrodes, the electrodes including an anode and cathode, at least one of the electrodes containing fluorine, wherein said anode comprises a material selected from the group consisting of a metal, a metal alloy, a metal oxide, a metal fluoride, an alloy metal fluoride, a metal oxide fluoride, a polyaniline, and a polypyrrole, and wherein said cathode comprises a material selected from the group consisting of a metal, a metal alloy, a metal oxide, a metal fluoride, an alloy metal fluoride, a metal oxide fluoride, a polyaniline, and a polypyrrole; wherein said cathode and said anode comprise different materials; and
a lithium-free electrolyte comprising an organic-soluble fluoride salt dissolved in a solvent, wherein the electrolyte is a liquid; wherein said organic-soluble fluoride salt comprises a fluorine-substituted or unsubstituted alkylammonium cation having the formula: $R^1R^2R^3R^4N^+$ or a fluorine-substituted or unsubstituted alkylphosphonium cation having the formula: $R^1R^2R^3R^4P^+$; wherein each of $R^1$, $R^2$, $R^3$ and $R^4$ is independently a fluorine-substituted or unsubstituted $C_1$ to $C_{50}$ aliphatic group, a $C_1$ to $C_{50}$ cyclic aliphatic group, a $C_1$ to $C_{50}$ fluoroalkyl group, a $C_1$ to $C_{50}$ oligo(ethyleneglycol) group, a $C_1$ to $C_{50}$ alkyl group, or a $C_4$ to $C_{50}$ aryl group; and wherein at least one of $R^1$, $R^2$, $R^3$ and $R^4$ is said $C_1$ to $C_{50}$ alkyl group.

2. The fluoride ion battery of claim 1, wherein said solvent is selected from the group of acetonitrile, benzonitrile, 4-fluorobenzonitrile, pentafluorobenzonitrile, triethylamine, diisopropylethylamine, 1,2-dimethoxyethane, ethylene carbonate, propylene carbonate, γ-butyrolactone, dimethyl carbonate, diethyl carbonate, methyl ethyl carbonate, propyl methyl carbonate, tetrahydrofuran, 2-methyltetrahydrofuran, nitromethane, benzene, toluene, chloroform, dichloromethane, 1,2-dichloroethane, dimethylsulfoxide, sulfolane, N,N-dimethylformamide, N,N-dimethylacetamide, carbon disulfide, ethyl acetate, methyl butyrate, n-propyl acetate, methyl propionate, methyl formate, 4-methyl-1,3,-dioxolane, pyridine, methyl isobutyl ketone, methyl ethyl ketone, hexamethylphosphoramide, hexamethylphosphorus triamide, 1-methyl-2-pyrrolidinone, 2-methoxyethyl acetate, sulfones, ethylmethylsulfone, trimethylene sulfone, 1-methyltrimethylene sulfone, ethyl-sec-butyl sulfone, 3,3,3-trifluoropropylmethyl sulfone and 2,2,2-trifluoroethyl sulfone.

3. The fluoride ion battery of claim 1, wherein the organic-soluble fluoride salt comprises said alkylammonium cation.

4. The fluoride ion battery of claim 1, wherein each of $R^1$, $R^2$, $R^3$ and $R^4$ is independently a $C_1$ to $C_{50}$ aliphatic group or a $C_4$ to $C_{50}$ aryl group.

5. The fluoride ion battery of claim 1, wherein the organic-soluble fluoride salt cation comprises said alkylphosphonium cation.

6. The fluoride ion battery of claim 5, wherein the organic-soluble fluoride salt is selected from the group consisting of: tetramethylphosphonium fluoride, tetraphenylphosphonium fluoride, and phenyltrimethylphosphonium fluoride.

7. The fluoride ion battery of claim 1, wherein the organic-soluble fluoride salt is selected from the group consisting of: tetramethylammonium fluoride, 2,2-dimethylpropyltrimethylammonium fluoride, 1-adamantyltrimethylammonium fluoride, and phenyltrimethylammonium fluoride.

8. The fluoride ion battery of claim 1, wherein the cathode comprises fluorine.

9. The fluoride ion battery of claim 1, wherein the anode comprises fluorine.

10. The fluoride ion battery of claim 1, wherein the cathode comprises a material selected from the group of a metal, a metal alloy, and a metal oxide.

11. The fluoride ion battery of claim 1, wherein the anode comprises a material selected from the group of a metal, a metal alloy, and a metal oxide.

12. The fluoride ion battery of claim 1, wherein the fluoride ion battery is rechargeable, the electrochemical reactions between the anode and the cathode being reversible.

13. The fluoride ion battery of claim 1, wherein the fluoride ion battery is a primary battery, the electrochemical reactions between the anode and the cathode being substantially irreversible.

14. The fluoride ion battery of claim 1, wherein the solvent is selected from the group consisting of: nitriles, amines, ethers, carbonates, nitro compounds, aliphatic and aromatic hydrocarbons, halogenated compounds, sulfoxides, sulfones, amides, esters, alcohols, and heterocyclic compounds.

15. The fluoride ion battery of claim 1, wherein the electrolyte is said liquid at a temperature greater than −40 degrees Celsius and less than 200 degrees Celsius.

16. The fluoride ion battery of claim 1, wherein the electrolyte is said liquid at a temperature greater than −40 degrees Celsius and less than 100 degrees Celsius.

17. The fluoride ion battery of claim 1, wherein the solvent is a nonaqueous solvent.

18. The fluoride ion battery of claim 1, wherein the solvent is an organic solvent.

19. The fluoride ion battery of claim 1, wherein said anode material comprises Ca, Ce, La, or Ba.

20. The fluoride ion battery of claim 1, wherein said cathode material comprises $BiF_3$, $CuF_2$, $CoF_3$, $SnF_2$, or $FeF_3$.

21. The fluoride ion battery of claim 1, wherein said anode and said cathode are a pair selected from the group consisting of: La/$CoF_3$, Ca/$CoF_3$, La/$CuF_2$, Ca/$CuF_2$, and La/$BiF_3$.

* * * * *